(12) United States Patent
Kripp et al.

(10) Patent No.: US 10,000,720 B2
(45) Date of Patent: Jun. 19, 2018

(54) LUBRICANT COMPOSITIONS CONTAINING BETA-GLUCANS

(71) Applicants: BASF SE, Ludwigshafen (DE); Wintershall Holding GmbH, Kassel (DE)

(72) Inventors: Reiner Kripp, Ludwigshafen (DE); Andrea Seibert, Griescheim (DE); Dirk Fries, Flörsheim-Dalsheim (DE); Achim Feβenbecker, Waghäusel (DE); Thomas Ruehle, Mannheim (DE)

(73) Assignees: BASF SE, Ludwigshafen (DE); Wintershall Holding GmbH, Kassel (DE)

( * ) Notice: Subject to any disclaimer, the term of this patent is extended or adjusted under 35 U.S.C. 154(b) by 0 days. days.

(21) Appl. No.: 15/312,855

(22) PCT Filed: May 19, 2015

(86) PCT No.: PCT/EP2015/060995
§ 371 (c)(1),
(2) Date: Nov. 21, 2016

(87) PCT Pub. No.: WO2015/177150
PCT Pub. Date: Nov. 26, 2015

(65) Prior Publication Data
US 2017/0183600 A1   Jun. 29, 2017

(30) Foreign Application Priority Data

May 22, 2014  (EP) ..................................... 14169478

(51) Int. Cl.
*C10M 145/40* (2006.01)
*C12P 19/04* (2006.01)

(52) U.S. Cl.
CPC ........... *C10M 145/40* (2013.01); *C12P 19/04* (2013.01); *C10M 2201/02* (2013.01); *C10M 2207/2835* (2013.01); *C10M 2209/12* (2013.01); *C10N 2230/02* (2013.01); *C10N 2230/04* (2013.01); *C10N 2230/06* (2013.01); *C10N 2230/10* (2013.01); *C10N 2230/12* (2013.01); *C10N 2230/14* (2013.01); *C10N 2230/18* (2013.01); *C10N 2230/36* (2013.01); *C10N 2240/08* (2013.01)

(58) Field of Classification Search
CPC ........... C10M 145/40; C10M 2201/02; C10M 2207/2835; C10M 2209/12; C12P 19/04; C10N 2230/02; C10N 2230/04; C10N 2230/06; C10N 2230/08; C10N 2230/10; C10N 2230/12; C10N 2230/14; C10N 2230/18; C10N 2230/36; C10N 2240/08
See application file for complete search history.

(56) References Cited

U.S. PATENT DOCUMENTS

| | | |
|---|---|---|
| 3,087,936 A | 4/1963 | Le Suer |
| 3,149,178 A | 9/1964 | Hamilton et al. |
| 3,172,892 A | 3/1965 | Le Suer et al. |
| 3,254,025 A | 5/1966 | Le Suer |
| 3,381,022 A | 4/1968 | Le Suer |
| 3,382,291 A | 5/1968 | Brennan |
| 3,742,082 A | 6/1973 | Brennan |
| 3,769,363 A | 10/1973 | Brennan |
| 3,876,720 A | 4/1975 | Heilman et al. |
| 4,149,178 A | 4/1979 | Estes |
| 4,234,435 A | 11/1980 | Meinhardt et al. |
| 4,239,930 A | 12/1980 | Allphin et al. |
| 4,367,352 A | 1/1983 | Watts, Jr. et al. |
| 4,413,156 A | 11/1983 | Watts, Jr. et al. |
| 4,434,308 A | 2/1984 | Larkin |
| 4,434,408 A | 2/1984 | Baba et al. |
| 4,910,355 A | 3/1990 | Shubkin et al. |
| 4,956,122 A | 9/1990 | Watts et al. |
| 5,068,487 A | 11/1991 | Theriot |
| 5,135,638 A | 8/1992 | Miller |
| 5,246,566 A | 9/1993 | Miller |
| 5,362,378 A | 11/1994 | Borghard et al. |
| 5,565,086 A | 10/1996 | Cody et al. |
| 6,303,533 B1 | 10/2001 | Grosch et al. |
| 6,342,486 B1 | 1/2002 | Zülli et al. |
| 6,933,263 B2 * | 8/2005 | Manka ................. C10M 171/00 508/154 |

(Continued)

FOREIGN PATENT DOCUMENTS

| | | |
|---|---|---|
| CA | 2063490 A1 | 9/1992 |
| CA | 1329159 C | 5/1994 |

(Continued)

OTHER PUBLICATIONS

U.S. Appl. No. 15/039,594, filed May 26, 2016, Rettemeyer et al.
U.S. Appl. No. 15/114,910, filed Jul. 28, 2016, Kashani-Shirazi et al.
International Search Report for PCT/EP2015/060995 dated Jul. 24, 2015.

*Primary Examiner* — James Goloboy

(74) *Attorney, Agent, or Firm* — Drinker Biddle & Reath LLP

(57) ABSTRACT

The presently claimed invention relates to a lubricant composition comprising at least one beta-glucan, optionally in form of one of its derivatives, at least one base oil, at least one additive component, and optionally water; the use of said lubricant compositions for reducing wear in metal-on-metal contact and the use of at least one beta-glucan for reducing the friction coefficient of a lubricant composition.

19 Claims, No Drawings

(56) References Cited

U.S. PATENT DOCUMENTS

| | | | | |
|---|---|---|---|---|
| 2010/0025290 A1* | 2/2010 | Feustel | .................. | C10L 10/16 |
| | | | | 208/14 |
| 2013/0109603 A1 | 5/2013 | Russo et al. | | |
| 2014/0000540 A1* | 1/2014 | Russo | .................... | C10L 10/08 |
| | | | | 123/1 A |

FOREIGN PATENT DOCUMENTS

| | | |
|---|---|---|
| DE | 4012238 A1 | 1/1991 |
| EP | 271907 A2 | 6/1988 |
| EP | 321302 A2 | 6/1989 |
| EP | 321304 A2 | 6/1989 |
| EP | 504673 A1 | 9/1992 |
| EP | 710710 A2 | 5/1996 |
| GB | 1500854 A | 2/1978 |
| WO | WO-2003016545 A2 | 2/2003 |
| WO | WO-2008014315 A2 | 1/2008 |

* cited by examiner

LUBRICANT COMPOSITIONS CONTAINING BETA-GLUCANS

CROSS-REFERENCE TO RELATED APPLICATIONS

This application is a national stage application (under 35 U.S.C. § 371) of PCT/EP2015/060995, filed May 19, 2015, which claims benefit of European Application No. 14169478.6, filed May 22, 2014, both of which are incorporated herein by reference in their entirety.

The presently claimed invention relates to a lubricant composition comprising at least one beta-glucan, optionally in form of one of its derivatives, at least one base oil, at least one additive component, and optionally water; the use of said lubricant compositions for reducing wear in metal-on-metal contact and the use of at least one beta-glucan for reducing the friction coefficient of a lubricant composition.

TECHNICAL BACKGROUND

New and advanced transmission systems are being developed by the automotive industry. These new systems often involve high energy requirements. Therefore, component protection technology must be developed to meet the increasing energy requirements of these advanced systems.

Extremely high metal-on-metal pressures are present in newer automatic and manual transmissions such as step automatic transmissions, continuously variable transmissions, manual or automated manual transmissions. High pressures are also present in various gear drive components such as automotive differentials and power transmission gear drive components. The high pressure present in such transmission and gear drive components mean that lubricant compositions used in these systems must be suitable for such extreme pressure applications to prevent wear and avoid seizure of the rotating and contacting components.

Thus, there continues to be a need for lubricant compositions which reduce wear while at the same time other advantageous properties of lubricating compositions such as good friction properties are retained.

Accordingly, it was an object of the presently claimed invention to provide a lubricant composition showing good fluidity—as expressed by a low friction coefficient of the lubricant composition—and excellent lubricity—as expressed by a low wear scar when using the lubricant composition in contact with rubbing surfaces.

DESCRIPTION OF THE INVENTION

Thus, in one embodiment the presently claimed invention is directed to a lubricant composition comprising
a) ≥0.01 to ≤10% by weight of at least one beta-glucan, optionally in form of one of its derivatives,
b) ≥70 to ≤99.99% by weight of at least one base oil selected from the group consisting of Group I mineral oils, Group II mineral oils, Group III mineral oils, Group IV oils and Group V oils,
c) ≥0.0 to ≤30% by weight of at least one additive component, and
d) ≥0.0 to ≤50% by weight water,
whereby the sum of the weight percentages of the components a), b), c) and d) adds up to 100% by weight.

Polysaccharides composed of glucose units are also known as glucans. The branched homopolysaccharides have a main chain composed of β-1,3-linked glucose units of which, statistically, about each third unit is β-1,6-glycosidically linked to a further glucose unit. Beta-glucans have thickening properties so that the viscosity of aqueous solutions containing such branched homopolysaccharides increases significantly which in turn results in a lower fluidity. For example, adding only 5 g of schizophyllan to 1 L water leads to an aqueous solution having a viscosity that is comparable to the viscosity of honey.

However, surprisingly it was found that the addition of a beta-glucan to a lubricant composition allows for retaining or even improving the fluidity of a lubricant composition while at the same time the lubricity could even be significantly improved.

By the term "lubricant composition", in the sense of the presently claimed invention, is meant a composition which is capable of reducing friction between surfaces.

Surprisingly it was found that the at least beta-glucan which is present in the inventively claimed lubricant composition does not degrade, i.e. is not cleaved, even after storage at ambient temperature, i.e. 25° C., for a period of preferably at least three months, more preferably at least six months and most preferably at least nine months. In general, as a result of cleavage, beta-glucans lose their ability to impart increased viscosity to a fluid. Thus, as the beta-glucans are not cleaved, the initial viscosity of the inventively claimed lubricant composition is maintained even after storage at ambient temperature, i.e. 25° C., for a period of preferably at least three months, more preferably at least six months and most preferably at least nine months, i.e. preferably the measured viscosity of the inventively claimed lubricant composition does not deviate more than ±5%, more preferably not more than ±3%, most preferably not more than ±1%, from the initial viscosity of the inventively claimed lubricant composition, even after storage at ambient temperature, i.e. 25° C., for a period of preferably at least three months, more preferably at least six months and most preferably at least nine months.

Thus, preferably, the inventively claimed lubricant composition does not contain any compound selected from the group consisting of bactericides, lactic acid, lactate and 1,2-pentanediol; more preferably the inventively claimed lubricant composition does not contain any bactericide. For the purposes of the presently claimed invention, the term "bactericide" is defined as any product, agent or substance being capable of inhibiting and/or preventing the growth of bacteria.

Preferably the lubricant composition comprises ≥0.1 to ≤50% by weight water, more preferably ≥0.1 to ≤40% by weight water, even more preferably ≥0.1 to ≤30% by weight water, most preferably ≥0.1 to ≤10% by weight water and in particular ≥0.1 to ≤5% or ≥0.1 to ≤1% by weight water, related to the overall weight of the lubricant composition.

Preferably the lubricant composition comprises ≥0.01 to ≤1% by weight of at least one beta-glucan, optionally in form of one of its derivatives, more preferably ≥0.01 to ≤0.50% by weight of at least one beta-glucan, optionally in form of one of its derivatives, even more preferably ≥0.01 to ≤0.40% by weight of at least one beta-glucan, optionally in form of one of its derivatives, most preferably ≥0.05 to ≤0.35% by weight of at least one beta-glucan, optionally in form of one of its derivatives, and in particular ≥0.04 to ≤0.30% by weight of at least one beta-glucan, optionally in form of one of its derivatives, in each case related to the overall weight of the lubricant composition.

In order to avoid any turbidity of the inventively claimed lubricant composition, the at least one beta-glucan is present in the lubricant composition in completely dissolved form, i.e. after filtration of the lubricant composition by using a PTFE-45/25 filter (pore size 0.45 μm) there are not any particles left on the filter membrane.

Beta-glucans are a heterogeneous group of glucose polymers found in the cell walls of plants, bacteria and fungi. The common basic structural unit in beta-glucan as described herein is a backbone chain and side chains comprising or consisting of beta (1-3) linked glucosyl units. Depending on the source and the method of isolation, beta-glucans have various degrees of branching and linkages in the side chains.

Generally, in context with the presently claimed invention, the beta-glucan as described herein may be any beta-glucan such as beta-1,4-glucans, beta-1,3-glucans, beta-1,6-glucans and beta-1,3(1,6)-glucans. In one embodiment, the beta-glucan is a polymer consisting of a linear main chain of beta-D-(1-3)-glucopyranosyl units having a single beta-D-glucopyranosyl unit (1-6) linked to a beta-D-glucopyranosyl unit of the linear main chain with an average branching degree of about 0.3. In context with the presently claimed invention, the term "average branching degree about 0.3" may mean that in average about 3 of 10 beta-D-(1-3)-glucopyranosyl units are (1-6) linked to a single beta-D-glucopyranosyl unit. In this context, the term "about" may mean that the average branching degree may be within the range from 0.25 to 0.35, preferably from 0.25 to 0.33, more preferably from 0.27 to 0.33, most preferably from 0.3 to 0.33. It may also be 0.3 or 0.33. Schizophyllan, scleroglucan, paramylon, pachyman, cellulose, chitin, curdlan, laminarin, chrysolaminarin, lentinan, lichenin, pleuran and zymosan all have an average branching degree between 0.25 and 0.33 (Novak, loc cit, Survase, loc cit); for example, scleroglucan and schizophyllan have an average branching degree of 0.3 to 0.33. The average branching degree of a beta-glucan can be determined by methods known in the art, e.g., by periodic oxidation analysis, methylated sugar analysis and NMR (Brigand, Industrial Gums, Academic Press, New York/USA (1993), 461-472).

Preferably the beta-glucan as described herein is selected from the group consisting of schizophyllan, scleroglucan, paramylon, pachyman, cellulose, chitin, curdlan, laminarin, chrysolaminarin, lentinan, lichenin, pleuran and zymosan. More preferably, the beta-glucan is schizophyllan or scleroglucan, most preferably schizophyllan.

Schizophyllan and scleroglucan can both be referred to as scleroglucans. Scleroglucans as described herein are also referred to as beta-1,3(1,6)-glucans or beta-1,3-scleroglucans. The polysaccharide chains usually form a three-dimensional structure of triple helices; polymer chains consist of glucose units whose hydroxy groups in 1- and 3-position are beta-linked to form the polymer main chain, and wherein each third glucose unit contains in position 6 a further glucose moiety linked by its hydroxyl function in position 1 (beta-1,3-bonded glucopyranose as the main chain and beta-1,6-bonded glucopyranose as side chains) and has the structural formula:

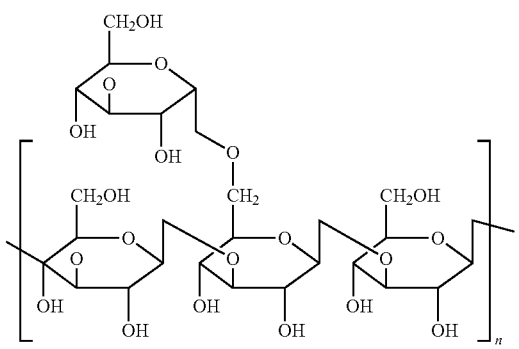

wherein n is a number which provides the beta-1,3-scleroglucan component with a weight average molecular weight (Mw) of $1 \cdot 10^6$ g/mol to $12 \cdot 10^6$ g/mol, preferably $2 \cdot 10^6$ g/mol to $10 \cdot 10^6$ g/mol. All weight average molecular weights (Mw) are determined from the readily measured Staudinger index rl using the following Mark-Houwink equation:

$$Mw = [\eta/4 \cdot 45 \cdot 10^{-7}]^{1/1.49}.$$

The beta-glucans as described herein is derived from any known source including but not limited to yeast, fungi, algae, grasses, moss, bacteria, seaweed and poaceae (gramineae) such as but not limited to oat, wheat, corn, millet and barnley.

Curdlan is derived from *Agrobacterium biobar*, a non-pathogenic bacteria. Zymosan is derived from yeast. Laminarin is obtained from brown algae, chrysolaminarin is derived from photosynthetic heterokonts and pleuran is derived from *Pleurotus ostreatus*. Lentinan is obtained from shiitake (*Lentinula edodes*) mushroom. Lichenan (moss starch) is obtained from mosses such as *Cetraria islandica*.

Scleroglucan-secreting strains of fungi are known to those skilled in the art. The strains of fungi are preferably selected from the group consisting of *Schizophyllum commune*, *Sclerotium rolfsii*, *Sclerotium glucanicum*, *Monilinia fructigena*, *Lentinula edodes* and *Botrytis cinera*. Suitable strains of fungi are also mentioned, for example, in EP 271 907 A2 and EP 504 673 A1, in each case claim 1. The strain of fungus used to produce the inventively used beta-glucan is particularly preferably *Schizophyllum commune* or *Sclerotium rolfsii* and very particularly preferably *Schizophyllum commune*. This strain of fungus secretes a glucan in which, on a main chain composed of β-1,3-glycosidically linked glucose units, each third unit, statistically, of the main chain is β-1,6-glycosidically linked to a further glucose unit; i.e. the glucan is preferably schizophyllan.

Processes for the fermentation of such strains of fungi are known in principle to those skilled in the art, for example from EP 271 907 A2, EP 504 673 A1, DE 40 12 238 A1, WO 2003/016545 A2 and also "Udo Rau, "Biosynthese, Produktion und Eigenschaften von extrazellularen PilzGlucanen", Habilitationsschrift, Technical University of Braunschweig, 1997", which in each case also mention suitable nutrient media. The fermentation systems may be continuous or batchwise systems.

The fermentation broth is obtained by fermenting fungi in a suitable aqueous nutrient medium. During the course of the fermentation, the fungi secrete the abovementioned class of glucans into the aqueous fermentation broth.

An aqueous solution comprising beta-glucans is ultimately removed from the fermentation broth which comprises dissolved beta-glucans and biomass (i.e. cell debris and/or other cellular components which accumulated during fermentation), leaving an aqueous fermentation broth in which the biomass has a higher concentration than before. The removal can especially be effected by means of single-stage or multistage filtration, or by means of centrifugation. It will be appreciated that it is also possible to combine several removal steps with one another.

The filtration can preferably be undertaken by means of crossflow filtration, especially crossflow microfiltration. The crossflow microfiltration process is known in principle to the person skilled in the art and is described, for example, in "Melin, Rautenbach, Membranverfahren [Membrane processes], Springer-Verlag, 3rd edition, 2007, page 309 to page 366". "Microfiltration" is understood by the person skilled in the art here to mean the removal of particles of a size between approx. 0.1 μm and approx. 10 μm.

After separating beta-glucan from the biomass the beta-glucan is removed from the aqueous solution and isolated in solid form, for example by precipitation by means of suitable solvent, followed by drying. Furthermore, for economic reasons, it may be sensible to concentrate the aqueous beta-glucan solution to be precipitated before contacting it with any precipitating agent. This can be performed by several methods known in the art such as, e.g., evaporation, ultracentrifugation, ultrafiltration, nanofiltration, reverse osmosis, precipitation, extraction, adsorption or freezing out.

In a preferred embodiment, the beta-glucan that is used in the inventively claimed lubricant composition does not contain any cell debris and/or cellular components.

In a preferred embodiment, the beta-glucan is present in the inventively claimed lubricant composition in the form of one of its derivatives.

Beta-glucans that are used in the inventively claimed lubricant composition can be derivatised, i.e. the chemical structure of the beta-glucan is altered as compared to its naturally occurring state. A beta-glucan in the form of its derivative preferably contains a chemical moiety selected from the group consisting of sulfate, amine, acetate, phosphate, phosphonate and carboxymethyl. Beta-glucans which are present in the form of their carboxymethylated derivatives are inter alia described in U.S. Pat. No. 6,342,486. The disclosure of U.S. Pat. No. 6,342,486 is hereby incorporated by reference.

A beta-glucan such as schizophyllan may be converted into the form of its derivative by oxidation, enzyme conversion, acid hydrolysis, heat and/or acid dextrinization or shear. The beta-glucan such as schizophyllan can also be chemically, enzymatically or physically modified. Suitable chemical derivatives of schizophyllan include esters, such as the acetate and half esters, such as the succinate, octenyl succinate and tetradecenyl succinate, phosphate derivatives, ethers such as hydroxyalkyl ethers and cationic ethers, or any other derivatives or combinations thereof. Modification may also be chemical crosslinking. Crosslinking agents that are suitable for use herein include phosphorus oxychloride, epichlorohydrin, sodium trimetaphosphate and adipic acid/acetic acid mixed anhydrides.

Preferably the inventively claimed lubricant composition comprises ≥80 to ≤99.9% by weight, more preferably ≥85 to ≤99.5% by weight, of at least one base oil selected from the group consisting of Group I mineral oils, Group II mineral oils, Group III mineral oils, Group IV oils and Group V oils, related to the overall weight of the lubricant composition.

The inventively claimed lubricant composition comprises base oils selected from the group consisting of mineral oils (Group I, II or III oils), polyalphaolefins (Group IV oils), polymerized and interpolymerized olefins, alkyl naphthalenes, alkylene oxide polymers, silicone oils, phosphate esters and carboxylic acid esters (Group V oils). The base oil (or base stock) to be used in the lubricant compositions according to the present invention is an inert, solvent-type oil component in the lubricant compositions according to the present invention.

The kinematic viscosity of the base oil at 40° C. is preferably from 2 to 3200 mm$^2$/s as determined in accordance with DIN 51562. In a more preferred embodiment, the base oil has a kinematic viscosity of 5 to 2000 mm$^2$/s, still more preferably 10 to 1000 mm$^2$/s, most preferably 10 to 100 mm$^2$/s and in particular 20 to 60 mm$^2$/s, in each case as determined in accordance with DIN 51562.

Definitions for the base oils according to the present invention are the same as those found in the American Petroleum Institute (API) publication "Engine Oil Licensing and Certification System", Industry Services Department, Fourteenth Edition, December 1996, Addendum 1, December 1998. Said publication categorizes base stocks as follows:

a) Group I base oils contain less than 90 percent saturates and/or greater than 0.03 percent sulfur and have a viscosity index greater than or equal to 80 and less than 120 using the test methods specified in the following table.
b) Group II base oils contain greater than or equal to 90 percent saturates and less than or equal to 0.03 percent sulfur and have a viscosity index greater than or equal to 80 and less than 120 using the test methods specified in the following table.
c) Group III base oils contain greater than or equal to 90 percent saturates and less than or equal to 0.03 percent sulfur and have a viscosity index greater than or equal to 120 using the test methods specified in the following table Analytical Methods for Base Stock:

| Property | Test Method |
|---|---|
| Saturates | ASTM D 2007 |
| Viscosity Index | ASTM D 2270 |
| Sulfur | ASTM D 2622 |
|  | ASTM D 4294 |
|  | ASTM D 4927 |
|  | ASTM D 3120 | d) Group IV base oils contain polyalphaolefins. Synthetic lower viscosity fluids suitable for the present invention include the polyalphaolefins (PAOs) and the synthetic oils from the hydrocracking or hydro-isomerization of Fischer Tropsch high boiling fractions including waxes. These are both base oils comprised of saturates with low impurity levels consistent with their synthetic origin. The hydro-isomerized Fischer Tropsch waxes are highly suitable base oils, comprising saturated components of iso-paraffinic character (resulting from the isomerization of the predominantly n-paraffins of the Fischer Tropsch waxes) which give a good blend of high viscosity index and low pour point. Processes for the hydro-isomerization of Fischer Tropsch waxes are described in U.S. Pat. Nos. 5,362,378; 5,565,086; 5,246,566 and 5,135,638, as well in EP 710710, EP 321302 and EP 321304.

Polyalphaolefins suitable for the lubricant compositions according to the present invention, include known PAO materials which typically comprise relatively low molecular weight hydrogenated polymers or oligomers of alphaolefins which include but are not limited to $C_2$ to about $C_{32}$ alphaolefins with the $C_8$ to about $C_{16}$ alphaolefins, such as 1-octene, 1-decene, 1-dodecene and the like being preferred.

The preferred polyalphaolefins are poly-1-octene, poly-1-decene, and poly-1-dodecene, although the dimers of higher olefins in the range of $C_{14}$ to $C_{18}$ provide low viscosity base stocks.

Terms like PAO 4, PAO 6 or PAO 8 are commonly used specifications for different classes of polyalphaolefins characterized by their respective viscosity. For instance, PAO 6 refers to the class of polyalphaolefins which typically has viscosity in the range of 6 mm$^2$/s at 100° C. A variety of commercially available compositions are available for these specifications.

Low viscosity PAO fluids suitable for the lubricant compositions according to the present invention, may be conveniently made by the polymerization of an alphaolefin in the presence of a polymerization catalyst such as the Friedel-Crafts catalysts including, for example, aluminum trichloride, boron trifluoride or complexes of boron trifluoride with water, alcohols such as ethanol, propanol or butanol, carboxylic acids or esters such as ethyl acetate or ethyl propionate. For example, the methods disclosed by U.S. Pat. No. 3,149,178 or 3,382,291 may be conveniently used herein. Other descriptions of PAO synthesis are found in the following U.S. Pat. No. 3,742,082 (Brennan); U.S. Pat. No. 3,769,363 (Brennan); U.S. Pat. No. 3,876,720 (Heilman); U.S. Pat. No. 4,239,930 (Allphin); U.S. Pat. No. 4,367,352 (Watts); U.S. Pat. No. 4,413,156 (Watts); U.S. Pat. No. 4,434,308 (Larkin); U.S. Pat. No. 4,910,355 (Shubkin); U.S. Pat. No. 4,956,122 (Watts); and U.S. Pat. No. 5,068,487 (Theriot).

e) Group V base oils contain any base stocks not described by Groups I to IV. Examples of Group V base oils include carboxylic acid esters, alkyl naphthalenes, alkylene oxide polymers, silicone oils, and phosphate esters.

Synthetic base oils include hydrocarbon oils and halo-substituted hydrocarbon oils such as polymerized and inter-polymerized olefins (e.g., polypropylenes, propylene-isobutylene copolymers, chlorinated polybutylenes, poly(1-hexenes), poly(1-octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and derivative, analogs and homologs thereof.

Alkylene oxide polymers and interpolymers and derivatives thereof where the terminal hydroxyl groups have been modified by esterification, etherification, etc., constitute another class of known synthetic base oils. These are exemplified by polyoxyalkylene polymers prepared by polymerization of ethylene oxide or propylene oxide, and the alkyl and aryl ethers of polyoxyalkylene polymers (e.g., methyl-polyiso-propylene glycol ether having a molecular weight of 1000 or diphenyl ether of polyethylene glycol having a molecular weight of 1000 to 1500); and mono- and poly-carboxylic esters thereof, for example, the acetic acid esters, mixed $C_3$-$C_8$ fatty acid esters and $C_{13}$ Oxo acid diester of tetraethylene glycol.

Silicon-based oils such as the polyalkyl-, polyaryl-, polyalkoxy- or polyaryloxysilicone oils and silicate oils comprise another useful class of synthetic base oils; such base oils include tetraethyl silicate, tetraisopropyl silicate, tetra-(2-ethylhexyl)silicate, tetra-(4-methyl-2-ethylhexyl)silicate, tetra-(p-tert-butyl-phenyl) silicate, hexa-(4-methyl-2-ethylhexyl)disiloxane and poly(methylphenyl)siloxanes. Other synthetic base oils include liquid esters of phosphorouscontaining acids (e.g., tricresyl phosphate, trioctyl phosphate, diethyl ester of decylphosphonic acid) and polymeric tetrahydrofurans.

Preferably the carboxylic acid esters are monoesters, diesters, triesters or polyesters, more preferably esters of monohydric alcohols and monobasic acids, esters of dihydric and/or polyhydric alcohols and monobasic acids and esters of monhohydric alcohols and dibasic acids.

Monohydric alcohols that are usually employed comprise $C_1$-$C_{24}$, preferably $C_1$-$C_{12}$ and more preferably $C_1$-$C_8$ monohydric alcohols, and such alcohols may be straight-chain or branched, and either saturated or unsaturated. As specific examples of $C_1$-$C_{24}$ alcohols there may be mentioned methanol, ethanol, straight-chain or branched propanol, straight-chain or branched butanol, straight-chain or branched pentanol, straight-chain or branched hexanol, straight-chain or branched heptanol, straight-chain or branched octanol, straight-chain or branched nonanol, straight-chain or branched decanol, straight-chain or branched undecanol, straight-chain or branched dodecanol, straight-chain or branched tridecanol, straight-chain or branched tetradecanol, straight-chain or branched pentadecanol, straight-chain or branched hexadecanol, straight-chain or branched heptadecanol, straight-chain or branched octadecanol, straight-chain or branched nonadecanol, straight-chain or branched eicosanol, straight-chain or branched heneicosanol, straight-chain or branched tricosanol, straight-chain or branched tetracosanol, and mixtures thereof.

Dihydric alcohols that are usually employed comprise ethylene glycol, diethylene glycol, polyethylene glycol, propylene glycol, dipropylene glycol, polypropylene glycol, 1,3-propanediol, 1,2-propanediol, 1,3-butanediol, 1,4-butanediol, 2-methyl-1,2-propan-ediol, 2-methyl-1,3-propanediol, 1,2-pentanediol, 1,3-pentanediol, 1,4-pentanediol, 1,5-pentanediol, neopentyl glycol, and mixtures thereof.

Polyhydric alcohols that are usually employed comprise trimethylolpropane, ditrimethylolethane, trimethylolpropane, ditrimethylolpropane, glycerin, pentaerythritol, dipentaerythritol, tripentaerythritol and sorbitol.

Monobasic acids that are usually employed comprise C2-C24 fatty acids, and the fatty acids may be straight-chain or branched and either saturated or unsaturated. As specific examples there may be mentioned saturated fatty acids such as acetic acid, propionic acid, straight-chain or branched butanoic acid, straight-chain or branched pentanoic acid, straight-chain or branched hexanoic acid, straight-chain or branched heptanoic acid, straight-chain or branched octanoic acid, straight-chain or branched nonanoic acid, straight-chain or branched decanoic acid, straight-chain or branched undecanoic acid, straight-chain or branched dodecanoic acid, straight-chain or branched tridecanoic acid, straight-chain or branched tetradecanoic acid, straight-chain or branched pentadecanoic acid, straight-chain or branched hexadecanoic acid, straight-chain or branched heptadecanoic acid, straight-chain or branched octadecanoic acid, straight-chain or branched hydroxyoctadecanoic acid, straight-chain or branched nonadecanoic acid, straight-chain or branched eicosanoic acid, straight-chain or branched heneicosanoic acid, straight-chain or branched docosanoic acid, straight-chain or branched tricosanoic acid and straight-chain or branched tetracosanoic acid; unsaturated fatty acids such as acrylic acid, straight-chain or branched butenoic acid, straight-chain or branched pentenoic acid, straight-chain or branched hexenoic acid, straight-chain or branched heptenoic acid, straight-chain or branched octenoic acid, straight-chain or branched nonenoic acid, straight-chain or branched decenoic acid, straight-chain or branched undecenoic acid, straight-chain or branched dodecenoic acid, straight-chain or branched tridecenoic acid, straight-chain or branched tetradecenoic acid, straight-chain or branched pentadecenoic acid, straight-chain or branched hexadecenoic acid, straight-chain or branched heptadecenoic acid, straight-chain or branched octadecenoic acid, straight-chain or branched hydroxyoctadecenoic acid, straight-chain or branched nonadecenoic acid, straight-chain or branched eicosenoic acid, straight-chain or branched heneicosenoic acid, straight-chain or branched docosenoic acid, straight-chain or branched tricosenoic acid and straight-chain or branched tetracosenoic acid; and mixtures thereof.

Dibasic acids that are usually employed comprise $C_2$-$C_{16}$ dibasic acids. Such $C_2$-$C_{16}$ dibasic acids may be straight-chain or branched, and either saturated or unsaturated. As specific examples there may be mentioned ethanedioic acid, propanedioic acid, straight-chain or branched butanedioic acid, straight-chain or branched pentanedioic acid, straight-chain or branched hexanedioic acid, straight-chain or branched heptanedioic acid, straight-chain or branched octanedioic acid, straight-chain or branched nonanedioic acid, straight-chain or branched decanedioic acid, straight-chain or branched undecanedioic acid, straight-chain or branched dodecanedioic acid, straight-chain or branched tridecanedioic acid, straight-chain or branched tetradecanedioic acid, straight-chain or branched heptadecanedioic acid, straight-chain or branched hexadecanedioic acid, straight-chain or branched hexenedioic acid, straight-chain or branched heptenedioic acid, straight-chain or branched octenedioic acid, straight-chain or branched nonenedioic acid, straight-chain or branched decenedioic acid, straight-chain or branched undecenedioic acid, straight-chain or branched dodecenedioic acid, straight-chain or branched tridecenedioic acid, straight-chain or branched tetradecenedioic acid, straight-chain or branched heptadecenedioic acid, straight-chain or branched hexadecenedioic acid, and mixtures thereof.

The carboxylic acid esters may be total carboxylic acid esters wherein all of the hydroxyl groups of the dihydric alcohol and/or polyhydric alcohols are esterified, or they may be partial carboxylic acid esters wherein a portion of the hydroxyl groups remain as hydroxyl groups without esterification. The carboxylic acid esters may also be total carboxylic acid esters wherein all of the carboxyl groups of the polybasic acid are esterified, or they may be partial carboxylic acid esters wherein a portion of the carboxyl groups remain as carboxyl groups without esterification.

More preferably the carboxylic acid ester is selected from the group consisting of diisodecyl adipate, diisotridecyl adipate, trimethylolpropane caprylate and trimethylolpropane-trioleate.

In another aspect of this embodiment, the carboxylic acid is selected from the group consisting of di-(isopropylheptyl)-adipate (DPHA) and diisononyladipate (DNA).

Preferably the lubricant composition comprises ≥0.01 to ≤30% by weight of at least one additive component, more preferably ≥0.1 to ≤5% by weight of at least one additive component, more preferably ≥0.4 to ≤3 by weight of at least one additive component, in each case related to the overall weight of the lubricant composition.

The lubricant composition according to the present invention may further comprise an additive component. In a preferred embodiment, the additive component is selected from the group consisting of antioxidants, dispersants, foam inhibitors, demulsifiers, seal swelling agents, friction reducers, anti-wear agents, detergents, corrosion inhibitors, extreme pressure agents, metal deactivators, rust inhibitors, pour point depressants and mixtures thereof.

The additive component as used in the present invention also includes an additive package and/or performance additives.

The additive package as used in the present invention as well as the compounds relating to performance additives are considered mixtures of additives that are typically used in lubricant compositions in limited amounts for mechanically, physically or chemically stabilizing the lubricant compositions while special performance characteristics can be further established by the individual or combined presence of such selected additives.

Additive packages are separately defined in the present invention since a variety of such additive packages are commercially available and typically used in lubricant compositions. One such preferred additive package that is commercially available is marketed under the name Anglamol6004J®.

However, the individual components contained in the additive packages and/or the compounds further defined in the present invention as so-called performance additives include a larger number of different types of additives including dispersants, metal deactivators, detergents, extreme pressure agents (typically boron- and/or sulfur- and/or phosphorus-containing), anti-wear agents, antioxidants (such as hindered phenols, aminic antioxidants or molybdenum compounds), corrosion inhibitors, foam inhibitors, demulsifiers, pour point depressants, seal swelling agents, friction modifiers and mixtures thereof.

The additive component as the sum of all additives contained in the lubricant compositions according to the present invention also including all additives contained in an additive package or added separately is present in the lubricant compositions of the present invention in an amount of 0.1 to 20 wt. %, preferably 1 to 20 wt. %, such as 2 to 15 wt. %, and 3 to 12 wt. %.

Extreme pressure agents include compounds containing boron and/or sulfur and/or phosphorus. The extreme pressure agent may be present in the lubricant compositions at 0% by weight to 15% by weight, or 0.05% by weight to 10% by weight, or 0.1% by weight to 8% by weight of the lubricant composition.

In one embodiment according to the present invention, the extreme pressure agent is a sulfur-containing compound. In one embodiment, the sulfur-containing compound may be a sulfurised olefin, a polysulfide, or mixtures thereof. Examples of the sulfurised olefin include a sulfurised olefin derived from propylene, isobutylene, pentene; an organic sulfide and/or polysulfide including benzyldisulfide; bis-(chlorobenzyl) disulfide; dibutyl tetrasulfide; di-tertiary butyl polysulfide; and sulfurised methyl ester of oleic acid, a sulfurised alkylphenol, a sulfurised dipentene, a sulfurised terpene, a sulfurised Diels-Alder adduct, an alkyl sulphenyl N'N-dialkyl dithiocarbamates; or mixtures thereof.

In one embodiment the sulfurised olefin includes a sulfurised olefin derived from propylene, isobutylene, pentene or mixtures thereof.

In one embodiment according to the present invention, the extreme pressure agent sulfur-containing compound includes a dimercaptothiadiazole or derivative, or mixtures thereof. Examples of the dimercaptothiadiazole include compounds such as 2,5-dimercapto-1,3,4-thiadiazole or a hydrocarbyl-substituted 2,5-dimercapto-1,3,4-thiadiazole, or oligomers thereof. The oligomers of hydrocarbyl-substituted 2,5-dimercapto-1,3,4-thiadiazole typically form by forming a sulfur-sulfur bond between 2,5-dimercapto-1,3,4-thiadiazole units to form derivatives or oligomers of two or more of said thiadiazole units. Suitable 2,5-dimercapto-1,3, 4-thiadiazole derived compounds include for example 2,5-bis(tert-nonyldithio)-1,3,4-thiadiazole or 2-tert-nonyldithio-5-mercapto-1,3,4-thiadiazole. The number of carbon atoms on the hydrocarbyl substituents of the hydrocarbyl-substituted 2,5-dimercapto-1,3,4-thiadiazole typically include 1 to 30, or 2 to 20, or 3 to 16.

In one embodiment, the dimercaptothiadiazole may be a thiadiazole-functionalised dispersant. A detailed description of the thiadiazole-functionalised dispersant is described is paragraphs [0028] to [0052] of International Publication WO 2008/014315.

The thiadiazole-functionalised dispersant may be prepared by a method including heating, reacting or complexing a thiadiazole compound with a dispersant substrate. The thiadiazole compound may be covalently bonded, salted, complexed or otherwise solubilised with a dispersant, or mixtures thereof.

The relative amounts of the dispersant substrate and the thiadiazole used to prepare the thiadiazole-functionalised dispersant may vary. In one embodiment the thiadiazole compound is present at 0.1 to 10 parts by weight relative to 100 parts by weight of the dispersant substrate. In different embodiments the thiadiazole compound is present at greater than 0.1 to 9, or greater than 0.1 to less than 5, or 0.2 to less than 5: to 100 parts by weight of the dispersant substrate. The relative amounts of the thiadiazole compound to the dispersant substrate may also be expressed as (0.1-10):100, or (>0.1-9):100, (such as (>0.5-9):100), or (0.1 to less than 5): 100, or (0.2 to less than 5): 100.

In one embodiment the dispersant substrate is present at 0.1 to 10 parts by weight relative to 1 part by weight of the thiadiazole compound. In different embodiments the dispersant substrate is present at greater than 0.1 to 9, or greater than 0.1 to less than 5, or about 0.2 to less than 5: to 1 part by weight of the thiadiazole compound. The relative amounts of 1 the dispersant substrate to the thiadiazole compound may also be expressed as (0.1-10):1, or (>0.1-9):1, (such as (>0.5-9):1), or (0.1 to less than 5): 1, or (0.2 to less than 5): 1.

The thiadiazole-functionalised dispersant may be derived from a substrate that includes a succinimide dispersant (for example, N-substituted long chain alkenyl succinimides, typically a polyisobutylene succinimide), a Mannich dispersant, an ester-containing dispersant, a condensation product of a fatty hydrocarbyl monocarboxylic acylating agent with an amine or ammonia, an alkyl amino phenol dispersant, a hydrocarbyl-amine dispersant, a polyether dispersant, a polyetheramine dispersant, a viscosity modifier containing dispersant functionality (for example polymeric viscosity index modifiers containing dispersant functionality), or mixtures thereof. In one embodiment the dispersant substrate includes a succinimide dispersant, an ester-containing dispersant or a Mannich dispersant.

In one embodiment according to the present invention, the extreme pressure agent includes a boron-containing compound. The boron-containing compound includes a borate ester (which in some embodiments may also be referred to as a borated epoxide), a borated alcohol, a borated dispersant, a borated phospholipid or mixtures thereof. In one embodiment the boron-containing compound may be a borate ester or a borated alcohol.

The borate ester may be prepared by the reaction of a boron compound and at least one compound selected from epoxy compounds, halohydrin compounds, epihalohydrin compounds, alcohols and mixtures thereof. The alcohols include dihydric alcohols, trihydric alcohols or higher alcohols, with the proviso for one embodiment that hydroxyl groups are on adjacent carbon atoms, i.e., vicinal.

Boron compounds suitable for preparing the borate ester include the various forms selected from the group consisting of boric acid (including metaboric acid, orthoboric acid and tetraboric acid), boric oxide, boron trioxide and alkyl borates. The borate ester may also be prepared from boron halides.

In one embodiment suitable borate ester compounds include tripropyl borate, tributyl borate, tripentyl borate, trihexyl borate, triheptyl borate, trioctyl borate, trinonyl borate and tridecyl borate. In one embodiment the borate ester compounds include tributyl borate, tri-2-ethylhexyl borate or mixtures thereof.

In one embodiment, the boron-containing compound is a borated dispersant, typically derived from an N-substituted long chain alkenyl succinimide. In one embodiment the borated dispersant includes a polyisobutylene succinimide. Borated dispersants are described in more detail in U.S. Pat. No. 3,087,936; and U.S. Pat. No. 3,254,025.

In one embodiment the borated dispersant may be used in combination with a sulfur-containing compound or a borate ester.

In one embodiment the extreme pressure agent is other than a borated dispersant.

The number average molecular weight Mn (GPC; kg/mol) of the hydrocarbon from which the long chain alkenyl group was derived includes ranges of 350 to 5000, or 500 to 3000, or 550 to 1500. The long chain alkenyl group may have a number average molecular weight Mn of 550, or 750, or 950 to 1000.

The N-substituted long chain alkenyl succinimides are borated using a variety of agents including boric acid (for example, metaboric acid, orthoboric acid and tetraboric acid), boric oxide, boron trioxide, and alkyl borates. In one embodiment the borating agent is boric acid which may be used alone or in combination with other borating agents.

The borated dispersant may be prepared by blending the boron compound and the N-substituted long chain alkenyl succinimides and heating them at a suitable temperature, such as, 80° C. to 250° C., or 90° C. to 230° C., or 100° C. to 210° C., until the desired reaction has occurred. The molar ratio of the boron compounds to the N-substituted long chain alkenyl succinimides may have ranges including 10:1 to 1:4, or 4:1 to $1:3; or the molar ratio of the boron compounds to the N-substituted long chain alkenyl succinimides may be 1:2. Alternatively, the ratio of moles B:moles N (that is, atoms of B:atoms of N) in the borated dispersant may be 0.25:1 to 10:1 or 0.33:1 to 4:1 or 0.2:1 to 1.5:1, or 0.25:1 to 1.3:1 or 0.8:1 to 1.2:1 or about 0.5:1 An inert liquid may be used in performing the reaction. The liquid may include toluene, xylene, chlorobenzene, dimethylformamide or mixtures thereof.

In one embodiment, the additive component in the lubricant composition according to the present invention further includes a borated phospholipid. The borated phospholipid may be derived from boronation of a phospholipid (for example boronation may be carried out with boric acid). Phospholipids and lecithins are described in detail in Encyclopedia of Chemical Technology, Kirk and Othmer, 3rd Edition, in "Fats and Fatty Oils", Volume 9, pages 795-831 and in "Lecithins", Volume 14, pages 250-269.

The phospholipid may be any lipid containing a phosphoric acid, such as lecithin or cephalin, or derivatives thereof. Examples of phospholipids include phosphatidylcholine, phosphatidylserine, phosphatidylinositol, phosphatidyl-ethanolamine, phosphotidic acid and mixtures thereof.

The phospholipids may be glycerophospholipids, glycerol derivatives of the above list of phospholipids. Typically, the glycerophospholipids have one or two acyl, alkyl or alkenyl groups on a glycerol residue. The alkyl or alkenyl groups may contain 8 to 30, or 8 to 25, or 12 to 24 carbon atoms. Examples of suitable alkyl or alkenyl groups include octyl, dodecyl, hexadecyl, octadecyl, docosanyl, octenyl, dodecenyl, hexadecenyl and octadecenyl.

Phospholipids may be prepared synthetically or derived from natural sources. Synthetic phospholipids may be prepared by methods known to those in the art. Naturally derived phospholipids are often extracted by procedures known to those in the art. Phospholipids may be derived from animal or vegetable sources. A useful phospholipid is derived from sunflower seeds. The phospholipid typically contains 35% to 60% phosphatidylcholine, 20% to 35% phosphatidylinositol, 1% to 25% phosphatidic acid, and 10% to 25% phosphatidylethanolamine, wherein the percentages are by weight based on the total phospholipids. The fatty acid content may be 20% by weight to 30% by weight palmitic acid, 2% by weight to 10% by weight stearic acid, 15% by weight to 25% by weight oleic acid, and 40% by weight to 55% by weight linoleic acid.

In another embodiment, the performance additive in the lubricant compositions according to the present invention may include a friction modifier. A friction modifier is any material or materials that can alter the coefficient of friction of a surface lubricated by any lubricant or fluid containing such material(s). Friction modifiers, also known as friction reducers, or lubricity agents or oiliness agents, and other such agents that change the ability of base oils, formulated lubricant compositions, or functional fluids, to modify the coefficient of friction of a lubricated surface may be effectively used in combination with the base oils or lubricant compositions of the present invention if desired. Friction modifiers may include metal-containing compounds or materials as well as ashless compounds or materials, or mixtures thereof. Metal-containing friction modifiers may include metal salts or metal-ligand complexes where the metals may include alkali, alkaline earth, or transition group metals. Such metal-containing friction modifiers may also have low-ash characteristics. Transition metals may include Mo, Sb, Sn, Fe, Cu, Zn, and others. Ligands may include hydrocarbyl derivative of alcohols, polyols, glycerols, partial ester glycerols, thiols, carboxylates, carbamates, thiocarbamates, dithiocarbamates, phosphates, thiophosphates, dithiophosphates, amides, imides, amines, thiazoles, thiadiazoles, dithiazoles, diazoles, triazoles, and other polar molecular functional groups containing effective amounts of O, N, S, or P, individually or in combination. In particular, Mo-containing compounds can be particularly effective such as for example Mo-dithiocarbamates, Mo(DTC), Mo-dithiophosphates, Mo(DTP), Mo-amines, Mo (Am), Mo-alcoholates, Mo-alcohol-amides, and the like.

Ashless friction modifiers may also include lubricant materials that contain effective amounts of polar groups, for example, hydroxyl-containing hydrocarbyl base oils, glycerides, partial glycerides, glyceride derivatives, and the like. Polar groups in friction modifiers may include hydrocarbyl groups containing effective amounts of O, N, S, or P, individually or in combination. Other friction modifiers that may be particularly effective include, for example, salts (both ash-containing and ashless derivatives) of fatty acids, fatty alcohols, fatty amides, fatty esters, hydroxyl-containing carboxylates, and comparable synthetic long-chain hydrocarbyl acids, alcohols, amides, esters, hydroxy carboxylates, and the like. In some instances fatty organic acids, fatty amines, and sulfurized fatty acids may be used as suitable friction modifiers.

In one embodiment, the performance additive in the lubricant compositions according to the present invention may include phosphorus- or sulfur-containing anti-wear agents other than compounds described as an extreme pressure agent of the amine salt of a phosphoric acid ester described above. Examples of the anti-wear agent may include a non-ionic phosphorus compound (typically compounds having phosphorus atoms with an oxidation state of +3 or +5), a metal dialkyldithiophosphate (typically zinc dialkyldithiophosphates), amine dithiophosphate, ashless dithiophosphates and a metal mono- or di-alkylphosphate (typically zinc phosphates), or mixtures thereof.

The non-ionic phosphorus compound includes a phosphite ester, a phosphate ester, or mixtures thereof.

In one embodiment, the performance additive in the lubricant composition according to the present invention may further include at least one antioxidant. Antioxidants retard the oxidative degradation of base stocks during service. Such degradation may result in deposits on metal surfaces, the presence of sludge, or a viscosity increase in the lubricant. One skilled in the art knows a wide variety of oxidation inhibitors that are useful in lubricating oil compositions.

Antioxidants include phenolic antioxidants such as hindered phenolic antioxidants or non-phenolic oxidation inhibitors. Useful antioxidants include hindered phenols. These phenolic antioxidants may be ashless (metal-free) phenolic compounds or neutral or basic metal salts of certain phenolic compounds. Typical phenolic antioxidant compounds are the hindered phenolics which are the ones which contain a sterically hindered hydroxyl group, and these include those derivatives of dihydroxy aryl compounds in which the hydroxyl groups are in the o- or p-position to each other. Typical phenolic antioxidants include the hindered phenols substituted with $C_{6+}$ alkyl groups and the alkylene coupled derivatives of these hindered phenols. Examples of phenolic materials of this type 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; and 2-methyl-6-t-butyl-4-dodecyl phenol. Other useful hindered mono-phenolic antioxidants may include for example hindered 2,6-di-alkyl-phenolic propionic ester derivatives. Bis-phenolic antioxidants may also be advantageously used in combination with the instant invention. Examples of ortho-coupled phenols include: 2,2'-bis(4-heptyl-6-t-butyl-phenol); 2,2'-bis(4-octyl-6-t-butyl-phenol); and 2,2'-bis(4-dodecyl-6-t-butyl-phenol). Para-coupled bisphenols include for example 4,4'-bis (2,6-di-t-butyl phenol) and 4,4'-methylene-bis(2,6-di-t-butyl phenol).

Non-phenolic oxidation inhibitors which may be used include aromatic amine antioxidants and these may be used either as such or in combination with phenolics. Typical examples of non-phenolic antioxidants include: alkylated and non-alkylated aromatic amines such as aromatic monoamines of the formula $R^8R^9R^{10}N$, where $R^8$ is an aliphatic, aromatic or substituted aromatic group, $R^9$ is an aromatic or a substituted aromatic group, and $R^{10}$ is H, alkyl, aryl or $R^{11}S(O)_xR^{12}$, where $R^{11}$ is an alkylene, alkenylene, or aralkylene group, $R^{12}$ is a higher alkyl group, or an alkenyl, aryl, or alkaryl group, and x is 0, 1 or 2. The aliphatic group $R^8$ may contain from 1 to about 20 carbon atoms, and preferably contains from about 6 to 12 carbon atoms. The aliphatic group is a saturated aliphatic group. Preferably, both $R^8$ and $R^9$ are aromatic or substituted aromatic groups, and the aromatic group may be a fused ring aromatic group such as naphthyl. Aromatic groups $R^8$ and $R^9$ may be joined together with other groups such as S.

Typical aromatic amines antioxidants have alkyl substituent groups of at least about 6 carbon atoms. Examples of aliphatic groups include hexyl, heptyl, octyl, nonyl, and decyl. Generally, the aliphatic groups will not contain more than about 14 carbon atoms. The general types of amine antioxidants useful in the present compositions include diphenylamines, phenyl naphthylamines, phenothiazines, imidodibenzyls and diphenyl phenylene diamines. Mixtures of two or more aromatic amines are also useful. Polymeric amine antioxidants can also be used. Particular examples of aromatic amine antioxidants useful in the present invention include: p,p'-dioctyldiphenylamine; t-octylphenyl-alpha-naphthylamine; phenyl-alphanaphthylamine; and p-octyl-phenyl-alpha-naphthylamine. Sulfurized alkyl phenols and alkali or alkaline earth metal salts thereof also are useful antioxidants.

In one embodiment, the performance additive in the lubricant compositions according to the present invention further includes a dispersant. The dispersant may be a succinimide dispersant (for example N-substituted long chain alkenyl succinimides), a Mannich dispersant, an ester-containing dispersant, a condensation product of a fatty hydrocarbyl monocarboxylic acylating agent with an amine or ammonia, an alkyl amino phenol dispersant, a hydrocarbyl-amine dispersant, a polyether dispersant or a polyetheramine dispersant.

In one embodiment the succinimide dispersant includes a polyisobutylene-substituted succinimide, wherein the polyisobutylene from which the dispersant is derived may have a number average molecular weight of 400 to 5000, or 950 to 1600. Succinimide dispersants and their methods of preparation are more fully described in U.S. Pat. Nos. 4,234,435 and 3,172,892. Suitable ester-containing dispersants are typically high molecular weight esters. These materials are described in more detail in U.S. Pat. No. 3,381,022.

In one embodiment the dispersant includes a borated dispersant. Typically the borated dispersant includes a succinimide dispersant including a polyisobutylene succinimide, wherein the polyisobutylene from which the dispersant is derived may have a number average molecular weight of 400 to 5000. Borated dispersants are described in more detail above within the extreme pressure agent description.

Dispersant viscosity modifiers (often referred to as DVMs) are considered additives in the context of the present invention due to their additional functionalization and are therefore not considered viscosity improving agents according to the present invention. Dispersant viscosity modifiers include functionalised polyolefins, for example, ethylene-propylene copolymers that have been functionalized with the reaction product of maleic anhydride and an amine, a polymethacrylate functionalised with an amine, or esterified styrene maleic anhydride copolymers reacted with an amine.

As another type of performance additives, corrosion inhibitors can be described as any materials (additives, functionalized fluids, etc.) that form a protective film on a surface that prevents corrosion agents from reacting or attacking that surface with a resulting loss of surface material. Protective films may be absorbed on the surface or chemically bonded to the surface. Protective films may be constituted from mono-molecular species, oligomeric species, polymeric species, or mixtures thereof. Protective films may derive from the intact corrosion inhibitors, from their combination products, or their degradation products, or mixtures thereof. Surfaces that may benefit from the action of corrosion inhibitors may include metals and their alloys (both ferrous and non-ferrous types) and non-metals.

Corrosion inhibitors may include various oxygen-, nitrogen-, sulfur-, and phosphorus-containing materials, and may include metal-containing compounds (salts, organometallics, etc.) and nonmetal-containing or ashless materials. Corrosion inhibitors may include, but are not limited to, additive types such as, for example, hydrocarbyl-, aryl-, alkyl-, arylalkyl-, and alkylaryl-versions of detergents (neutral, overbased), sulfonates, phenates, salicylates, alcoholates, carboxylates, salixarates, phosphites, phosphates, thiophosphates, amines, amine salts, amine phosphoric acid salts, amine sulfonic acid salts, alkoxylated amines, ether-amines, polyetheramines, amides, imides, azoles, diazoles, triazoles, benzotriazoles, benzothiadoles, mercaptobenzothiazoles, tolyltriazoles (TTZ-type), heterocyclic amines, heterocyclic sulfides, thiazoles, thiadiazoles, mercaptothiadiazoles, dimercaptothiadiazoles (DMTD-type), imidazoles, benzimidazoles, dithiobenzimidazoles, imidazolines, oxazolines, Mannich reactions products, glycidyl ethers, anhydrides, carbamates, thiocarbamates, dithiocarbamates, polyglycols, etc., or mixtures thereof.

Corrosion inhibitors are used to reduce the degradation of metallic parts that are in contact with the lubricant composition. Suitable corrosion inhibitors include thiadiazoles. Aromatic triazoles, such as tolyltriazole, are suitable corrosion inhibitors for non-ferrous metals, such as copper.

Metal deactivators include derivatives of benzotriazoles (typically tolyltriazole), 1,2,4-triazoles, benzimidazoles, 2-alkyldithiobenzimidazoles, thiadiazoles or 2-alkyldithiobenzothiazoles.

Foam inhibitors may also advantageously be added as a performance additive to the lubricant compositions according to the present invention. These agents retard the formation of stable foams. Silicones and organic polymers are typical foam inhibitors. For example, polysiloxanes, such as silicon oil, or polydimethylsiloxane, provide foam inhibiting properties. Further foam inhibitors include copolymers of ethyl acrylate and 2-ethylhexyl acrylate and optionally vinyl acetate.

Demulsifiers include trialkyl phosphates, and various polymers and copolymers of ethylene glycol, ethylene oxide, propylene oxide, or mixtures thereof.

As pour point depressants, esters of maleic anhydride-styrene, or polyacrylamides are included.

As a further performance additive to be used in the lubricant compositions according to the present invention, seal compatibility agents help to swell elastomeric seals by causing a chemical reaction in the fluid or physical change in the elastomer. Suitable seal compatibility agents for lubricant compositions include organic phosphates, aromatic esters, aromatic hydrocarbons, esters (butylbenzyl phthalate, for example), and polybutenyl succinic anhydride. Such additives may preferably be used in an amount of 0.01 to 3% by weight, more preferably 0.01 to 2% by weight of the total amount of the lubricant composition.

In one embodiment, the lubricant composition according to the present invention may further include at least one viscosity index improver. The viscosity index improvers (VI improvers) include high molecular weight polymers that increase the relative viscosity of an oil at high temperatures more than they do at low temperatures. Viscosity index improvers (VI improvers) include polyacrylates, polymethacrylates, alkylmethacrylates, vinylpyrroliclone/methacrylate copolymers, poly vinylpyrrolidones, polybutenes, olefin copolymers such as an ethylene-propylene copolymer or a styrene-butadiene copolymer or polyalkene such as PIB, styrene/acrylate copolymers and polyethers, and combinations thereof. The most common VI improvers are methacrylate polymers and copolymers, acrylate polymers, olefin polymers and copolymers, and styrenebutadiene copolymers. Other examples of the viscosity index improver include polymethacrylate, polyisobutylene, alpha-olefin polymers, alpha-olefin copolymers (e.g., an ethylenepropylene copolymer), polyalkylstyrene, phenol condensates, naphthalene condensates, a styrenebutadiene copolymer and the like. Of these, polymethacrylate having a number average molecular weight of 10000 to 300000, and alpha-olefin polymers or alpha-olefin copolymers having a number average molecular weight of 1000 to 30000, particularly ethylene-alpha-olefin copolymers having a number average molecular weight of 1000 to 10000 are preferred.

The kinematic viscosity of the inventively claimed lubricant composition at 40° C. is preferably from 2 to 3200 $mm^2/s$ as determined in accordance with DIN 51562. In a more preferred embodiment, the base oil has a kinematic viscosity of 5 to 2000 $mm^2/s$, still more preferably 10 to 1000 $mm^2/s$, most preferably 10 to 300 $mm^2/s$ and in particular 10 to 100 $mm^2/s$, in each case as determined in accordance with DIN 51562.

In a preferred embodiment, the presently claimed invention is directed to a lubricant composition comprising
a) ≥0.01 to ≤1.0% by weight of at least one beta-glucan, optionally in form of one of its derivatives,
b) ≥70 to ≤99.99% by weight of at least one base oil selected from the group consisting of Group I mineral oils, Group II mineral oils, Group III mineral oils, Group IV oils and Group V oils,
c) ≥0.01 to ≤30% by weight of at least one additive component, and
d) ≥0.1 to ≤50% by weight water,
whereby the sum of the weight percentages of the components a), b), c) and d) adds up to 100% by weight.

In another preferred embodiment, the presently claimed invention is directed to a lubricant composition having a viscosity at 40° C. in the range of 2 to 3200 $mm^2/s$ as determined in accordance with DIN 51562 comprising
a) ≥0.01 to ≤1.0% by weight of at least one beta-glucan, optionally in form of one of its derivatives,
b) ≥70 to ≤99.99% by weight of at least one base oil selected from the group consisting of Group I mineral oils, Group II mineral oils, Group III mineral oils, Group IV oils and Group V oils, whereby the base oil has a viscosity at 40° C. in the range of 2 to 3200 $mm^2/s$ as determined in accordance with DIN 51562,
c) ≥0.01 to ≤30% by weight of at least one additive component, and
d) ≥0.1 to ≤50% by weight water,
whereby the sum of the weight percentages of the components a), b), c) and d) adds up to 100% by weight.

In another preferred embodiment, the presently claimed invention is directed to a lubricant composition having a viscosity at 40° C. in the range of 2 to 3200 $mm^2/s$ as determined in accordance with DIN 51562 comprising
a) ≥0.01 to ≤0.3% by weight of at least one beta-glucan, optionally in form of one of its derivatives,
b) ≥80 to ≤99.5% by weight of at least one base oil selected from the group consisting of Group I mineral oils, Group II mineral oils, Group III mineral oils, Group IV oils and Group V oils, whereby the base oil has a viscosity at 40° C. in the range of 2 to 3200 $mm^2/s$ as determined in accordance with DIN 51562,
c) ≥0.1 to ≤20% by weight of at least one additive component, and
d) ≥0.1 to ≤1% by weight water,
whereby the sum of the weight percentages of the components a), b), c) and d) adds up to 100% by weight.

The lubricant compositions and uses according to the invention may in one embodiment be implemented in the context of a light, medium and heavy duty engine oil, industrial engine oil, marine engine oil, automotive engine oil, crankshaft oil, compressor oil, refrigerator oil, hydrocarbon compressor oil, very low-temperature lubricating oil and fat, high temperature lubricating oil and fat, wire rope lubricant, textile machine oil, refrigerator oil, aviation and aerospace lubricant, aviation turbine oil, transmission oil, gas turbine oil, spindle oil, spin oil, traction fluid, transmission oil, plastic transmission oil, passenger car transmission oil, truck transmission oil, industrial transmission oil, industrial gear oil, insulating oil, instrument oil, brake fluid, transmission liquid, shock absorber oil, heat distribution medium oil, transformer oil, fat, chain oil, minimum quantity lubricant for metalworking operations, oil to the warm and cold working, oil for a water-based metalworking liquid, oil for a neat oil working fluid, oil for a semi-synthetic metalworking fluid, oil for a synthetic metalworking fluid, drilling detergent for the soil exploration, hydraulic oil, biodegradable lubricant or lubricating grease or wax, chain saw oil, release agent, moulding fluid, gun, pistol and rifle lubricant or watch lubricant and food grade approved lubricant.

In a preferred embodiment the lubricant composition is a metalworking fluid.

The kinematic viscosity of the metalworking fluid at 40° C. is preferably from 1 to 3200 $mm^2/s$ as determined in accordance with DIN 51562. In a more preferred embodiment, the base oil has a kinematic viscosity of 1 to 2000 $mm^2/s$, still more preferably 1 to 1000 $mm^2/s$, most preferably 1 to 300 $mm^2/s$ and in particular 1 to 100 $mm^2/s$, in each case as determined in accordance with DIN 51562.

The metalworking fluid according to the presently claimed invention is suitable for cutting, grinding, roll forming, forging, pressing, punching, rolling and the like. Increased improvement in properties for metalworking fluids are desired in the metalworking field from the viewpoint of working efficiency, tool life and handleability. The metalworking fluid can also be used as a lubricating oil for bearing sections, hydraulic equipment and gear sections, and therefore a single oil may be used as a general purpose oil for lubrication of each of these sections.

In a preferred embodiment, the presently claimed invention relates to the use of the inventive lubricant as a hydraulic oil, especially a biohydraulic oil. A hydraulic oil is used in hydraulic control sections that govern machine operations. Hydraulic oils show lubricating, sealing and cooling properties. In general, a hydraulic oil is used by compressing a lubricant composition at a high pressure with a pump to produce oil pressure and move equipment. Thus, hydraulic oils must have a high lubricity (wear resistance, seizing resistance etc.), a high oxidation stability and a high thermal stability.

A biohydraulic oil in the sense of the present invention is a biodegradable hydraulic oil. This is determined, for example, by the standard OECD 301 test or by the EPA 560/6-82-003 test, and preferably by OECD test 301 B. The biohydraulic oil shows a biological degradability of at least 60%, preferably at least 70% and, more particularly, at least 75%. This can be achieved according to the invention e.g. by employing the ester component in high amounts such as 80 to 99.9 wt. % in addition to the additive component in amounts of 0.1 to 20 wt. % in the absence of base oil component.

A gear section is a section that mainly accomplishes driving with a gear provided on a gear planer or the like. A gear oil is used for smooth gliding of the section for reduced metal-to-metal contact. Because a high load is applied onto the gear sliding surface, the gear oil must have good lubrication properties including high wear resistance and high seizing resistance.

The preferred embodiments as described above also apply to the uses and methods as outlined in the following passages.

In a another aspect, the presently claimed invention is directed to the use of a lubricating composition comprising
a) ≥0.01 to ≤10% by weight of at least one beta-glucan, optionally in form of one of its derivatives, and
b) ≥70 to ≤99.99% by weight of at least one base oil selected from the group consisting of Group I mineral oils, Group II mineral oils, Group III mineral oils, Group IV oils and Group V oils and/or water,
for reducing wear between rubbing surfaces of at least one first material and at least one second material, whereby the first and the second material are independently selected from the group consisting of metals, ceramics, fiber-reinforced composites, plastics and wood.

In a another aspect, the presently claimed invention is directed to the use of a lubricating composition comprising
a) ≥0.01 to ≤10% by weight of at least one beta-glucan, optionally in form of one of its derivatives,
b) ≥70 to ≤99.99% by weight of at least one base oil selected from the group consisting of Group I mineral oils, Group II mineral oils, Group III mineral oils, Group IV oils and Group V oils and/or water, and
c) ≥0.1 to ≤30% by weight of at least one additive component which is selected from the group consisting of antioxidants, dispersants, foam inhibitors, demulsifiers, seal swelling agents, friction reducers, anti-wear agents, detergents, corrosion inhibitors, extreme pressure agents, metal deactivators, rust inhibitors and pour point depressants,
for reducing wear between rubbing surfaces of at least one first material and at least one second material, whereby the first and the second material are independently selected from the group consisting of metals, ceramics, fiber-reinforced composites, plastics and wood.

In a another aspect, the presently claimed invention is directed to a method for reducing wear between rubbing surfaces of at least one first material and at least one second material, whereby the first and the second material are independently selected from the group consisting of metals, ceramics, fiber-reinforced composites, plastics and wood, comprising at least the step of applying a lubricant composition comprising
a) ≥0.01 to ≤10% by weight of at least one beta-glucan, optionally in form of one of its derivatives, and
b) ≥70 to ≤99.99% by weight of at least one base oil selected from the group consisting of Group I mineral oils, Group II mineral oils, Group III mineral oils, Group IV oils and Group V oils and/or water,
onto the at least one first material.

In a another aspect, the presently claimed invention is directed to a method for reducing wear between rubbing surfaces of at least one first material and at least one second material, whereby the first and the second material are independently selected from the group consisting of metals, ceramics, fiber-reinforced composites, plastics and wood, comprising at least the step of applying a lubricant composition comprising
a) ≥0.01 to ≤10% by weight of at least one beta-glucan, optionally in form of one of its derivatives,
b) ≥70 to ≤99.99% by weight of at least one base oil selected from the group consisting of Group I mineral oils, Group II mineral oils, Group III mineral oils, Group IV oils and Group V oils and/or water, and
c) ≥0.01 to ≤30% by weight of at least one additive component which is selected from the group consisting of antioxidants, dispersants, foam inhibitors, demulsifiers, seal swelling agents, friction reducers, anti-wear agents, detergents, corrosion inhibitors, extreme pressure agents, metal deactivators, rust inhibitors and pour point depressants,
onto the at least one first material.

In the sense of the presently claimed invention, the term "rubbing" refers to solid surfaces in frictional contact with each other.

The wear reduction achieved by using at least one beta-glucan is applicable to many types of solid surfaces in rubbing contact such as metals, ceramics, fiber-reinforced composites, plastics and wood.

Preferably the beta-glucans as described herein are used to reduce wear between mechanical parts in contact with each other, such as between gears, between a valve lifter and a cam of an automotive engine, and between a piston and cylinder in a motor. The beta-glucans as described herein can be used in lubricating and reducing wear of bearing (e.g. steel bearing, ceramic bearings). The beta-glucans as described herein can be used in machining and cutting operations to reduce wear of a machining/cutting tool (ceramic or metal) used in a machining operation such as lathing, broaching, tapping, threading, gear shaping, reaming, drilling, milling, hobbing, grinding and turning operations.

The materials that can be lubricated and experience wear reduction by the beta-glucans described herein and the inventively claimed method are not particularly limited and include materials such as ceramics, metals, composites, plastics, wood and combinations thereof. The rubbing surfaces involve tow (or more) contacting surfaces of solid materials. The contacting surfaces are in relative motion to each other. For example, confronting surfaces of two separate solid bodies can both be moving in sliding contact over one another, or alternatively, one surface can be stationary while another surface of another body is set in motion to slide in contact over the surface of the stationary body. Also, the inventively claimed method can be used to lubricate a plurality of metal surfaces in rubbing contact, a plurality of ceramic surfaces in rubbing contact or both a metal surface and a ceramic surface in rubbing contact.

Metals that can be lubricated according to the presently claimed invention comprise steel, alloy steels, alloy cast iron, aluminum alloys, titanium alloys and other advanced high strength, high temperature metallic alloys. Ceramic materials that can be lubricated according to the presently claimed invention comprise alumina, zirconia, silicon nitride, silicon carbide, boron nitride, aluminum nitride, boron carbide and beryllia. Polymer matrix composites (e.g. carbon fiber/epoxy, glass fiber/nylon, carbon/polyether ether ketone and high temperature polymeric composites) also serve as materials to be lubricated according to the presently claimed invention.

In another embodiment, the presently claimed invention is directed to the use of at least one beta-glucan as described herein for reducing the friction coefficient of a lubricant composition.

In yet another embodiment, the presently claimed invention is directed to a method for reducing the friction coefficient of a lubricant composition in the lubrication of a mechanical device comprising at least the step of formulating said lubricant composition with at least one beta-glucan as defined herein.

A person skilled in the art understands that the reduction of a friction coefficient of a lubricant composition leads to improved energy efficiency, i.e. a device that contains this lubricant composition can be operated with less energy consumption.

A mechanical device in the sense of the presently claimed invention is a mechanism consisting of a device that works on mechanical principles.

The mechanical device is preferably selected from the group consisting of bearings, gears, joints and guidances. Preferably the mechanical device is operated at temperatures in the range of ≥10° C. to ≤80° C.

Preferably the friction coefficient of the lubricant composition is determined with a high frequency reciprocating rig test according to DIN EN ISO 12156-1 at a load of 1000 g, a frequency of 2 mm/20 Hz, a fluid temperature of 60° C. and a test tube containing 2 mL lubricant composition.

EXAMPLES

Preparation of Schizophyllan

Schizophyllan was prepared by fermentation from *Schizophyllum commune* and subsequent separation of the biomass from schizophyllan by crossflow filtration. 5 g of acetone 50% w/w were added to an aqueous solution of schizophyllan. The mixture was mixed for 1 min in a vortex mixer and by hand shaking. During this, schizophyllan precipitates, which was then centrifuged off (2 min at 8500 rpm (10,000 g)), and the supernatant was decanted off. The schizophyllan was re-dissolved in waster. The aqueous mixture was dispersed for 2 min using Ultra-turrax (3800 rpm; T25 digital Ultra-Turrax from IKA). A mixture containing 26% by weight schizophyllan, 1% by weight acetone and 73% by weight water was obtained.

Preparation of Lubricant Compositions 100 mL of a fluid were thoroughly mixed with 1 mL of a mixture containing schizophyllan as prepared above (theoretical content of 0.25% by weight schizophyllan) for 0.5 hours at a temperature of 40° C. Schizophyllan did not dissolve completely in the fluid so that a turbid fluid was obtained. The turbid fluid containing schizophyllan was filtered with a PTFE-45/25 filter (pore size 0.45 μm) obtainable from Merck Millipore, Darmstadt, Germany.

The following compositions were prepared as described above:

Example 1: Trimethylolpropane Trioleate (Viscosity at 40° C. is 46 mm²/s as Determined in Accordance with DIN 51562, Obtainable as Synative® ES TMP 05 from BASF SE, Ludwigshafen) and Schizophyllan The viscosity of the composition was at 40° C. 50 mm²/s as determined in accordance with DIN 51562.

Example 2: A Water-Glycol Hydraulic Fluid (Viscosity at 40° C. is 41 mm²/s as Determined in Accordance with DIN 51562, Obtainable as Plurasafe® WGF 200 E from BASF SE, Ludwigshafen) and Schizophyllan The viscosity of the composition was at 40° C. 46 mm²/s as determined in accordance with DIN 51562.

Example 3 (for Illustrative Purposes): Distilled Water and Schizophyllan

The compositions according to examples 1 to 3 were subjected to a high frequency reciprocating rig test according to DIN EN ISO 12156-1 at a load of 1000 g, a frequency of 2 mm/20 Hz and a fluid temperature of 60° C. A 2 mL sample was used as the test fluid. The following results were obtained:

|  | Example 1 | Example 2 | Example 3 |
| --- | --- | --- | --- |
| Wear scar 1.4 [μm] | 157 | 164 | 362 |
| Film thickness [%] | 96 | 82 | 5 |
| Friction coefficient | 0.076 | 0.056 | 0.344 |

As comparative examples the composition was in each case tested without the presence of any schizophyllan.

|  | Comp. example 1 | Comp. example 2 | Comp. example 3 |
| --- | --- | --- | --- |
| Wear scar 1.4 [μm] | 174 | 192 | 781 |
| Film thickness [%] | 94 | 88 | 4 |
| Friction coefficient | 0.07 | 0.082 | 0.364 |

A low wear scar indicates the composition exhibits an improvement in lubricity. A high film thick-ness indicates that the composition exhibits low friction and low wear. A low friction coefficient indicates low friction.

Examples 1 to 3 show that the addition of schizophyllan in each case led to a significant improvement of the lubricity. In addition, examples 2 and 3 demonstrate that the addition of schizophyllan led to a significant improvement in both lubricity and friction properties.

The invention claimed is:
1. A lubricant composition comprising
   a) ≥0.01 to ≤10% by weight of at least one beta-glucan, optionally in form of one of its derivatives, and wherein the at least one beta-glucan is schizophyllan, scleroglucan, or zymosan,
   b) ≥70 to ≤99.99% by weight of at least one base oil selected from the group consisting of Group I mineral oils, Group II mineral oils, Group III mineral oils, Group IV oils and Group V oils,
   c) ≥0.0 to ≤30% by weight of at least one additive component, and
   d) ≥0.1 to ≤30% by weight water,
   whereby the sum of the weight percentages of the components a), b), c) and d) does not exceed 100% by weight and
   whereby the derivative of the at least one beta-glucan contains a chemical moiety selected from the group consisting of sulfate, amine, acetate, phosphate, phosphonate and carboxymethyl.
2. The lubricant composition according to claim 1, whereby the lubricant composition comprises ≥0.01 to

≤1.0% by weight of at least one beta-glucan, optionally in form of one of its derivatives.

3. The lubricant composition according to claim 1, whereby the lubricant composition comprises ≥80 to ≤99.9% by weight of at least one base oil selected from the group consisting of Group I mineral oils, Group II mineral oils, Group III mineral oils, Group IV oils and Group V oils.

4. The lubricant composition according to claim 1, whereby the lubricant composition comprises ≥0.01 to ≤30% by weight of at least one additive component.

5. A lubricant composition comprising
   a) ≥0.01 to ≤10% by weight of at least one beta-glucan, optionally in form of one of its derivatives, and wherein the at least one beta-glucan is schizophyllan, scleroglucan, or zymosan,
   b) ≥70 to ≤99.99% by weight of at least one base oil selected from the group consisting of Group I mineral oils, Group II mineral oils, Group III
   c) ≥0.0 to ≤30% by weight of at least one additive component, and
   d) ≥0.1 to ≤50% by weight water,
whereby the sum of the weight percentages of the components a), b), c) and d) does not exceed 100% by weight and wherein the at least one additive component is present and is selected from the group consisting of antioxidants, dispersants, foam inhibitors, demulsifiers, seal swelling agents, friction reducers, anti-wear agents, detergents, corrosion inhibitors, extreme pressure agents, metal deactivators, rust inhibitors and pour point depressants.

6. The lubricant composition according to claim 5, whereby the derivative of the at least one beta-glucan contains a chemical moiety selected from the group consisting of sulfate, amine, acetate, phosphate, phosphonate and carboxymethyl.

7. A lubricant composition comprising
   a) ≥0.01 to ≤10% by weight of at least one beta-glucan, optionally in form of one of its derivatives, and wherein the at least one beta-glucan is schizophyllan, scleroglucan, or zymosan,
   b) ≥70 to ≤99.99% by weight of at least one base oil selected from the group consisting of Group I mineral oils, Group II mineral oils, Group III mineral oils, Group IV oils and Group V oils,
   c) ≥0.0 to ≤30% by weight of at least one additive component, and
   d) ≥0.1 to ≤50% by weight water,
whereby the sum of the weight percentages of the components a), b), c) and d) does not exceed 100% by weight and whereby the lubricant composition has a viscosity at 40° C. in the range of 2 to 3200 mm$^2$/s as determined in accordance with DIN 51562.

8. A method for reducing wear between rubbing surfaces of at least one first material and at least one second material, whereby the first and the second material are independently selected from the group consisting of metals, ceramics, fiber-reinforced composites, plastics and wood,
   comprising at least the step of applying the lubricant according to claim 1 onto the at least one first material.

9. The method according to claim 8, whereby the at least one first material and the at least one second material consist of metal.

10. The lubricant composition according to claim 5, whereby the lubricant composition comprises ≥0.01 to ≤1.0% by weight of at least one beta-glucan, optionally in form of one of its derivatives.

11. The lubricant composition according to claim 5, whereby the lubricant composition comprises ≥80 to ≤99.9% by weight of at least one base oil selected from the group consisting of Group I mineral oils, Group II mineral oils, Group III mineral oils, Group IV oils and Group V oils.

12. The lubricant composition according to claim 5, whereby the lubricant composition comprises ≥0.01 to ≤30% by weight of at least one additive component.

13. The lubricant composition according to claim 7, whereby the lubricant composition comprises ≥0.01 to ≤1.0% by weight of at least one beta-glucan, optionally in form of one of its derivatives.

14. The lubricant composition according to claim 7, whereby the lubricant composition comprises ≥80 to ≤99.9% by weight of at least one base oil selected from the group consisting of Group I mineral oils, Group II mineral oils, Group III mineral oils, Group IV oils and Group V oils.

15. The lubricant composition according to claim 7, whereby the lubricant composition comprises ≥0.01 to ≤30% by weight of at least one additive component.

16. The lubricant composition according to claim 1, whereby the beta-glucan is schizophyllan.

17. The lubricant composition according to claim 7, whereby the beta-glucan is schizophyllan.

18. The lubricant composition according to claim 1, whereby the beta-glucan is scleroglucan.

19. The lubricant composition according to claim 1, whereby the beta-glucan is zymosan.

* * * * *